United States Patent
Ciupik

(10) Patent No.: US 10,299,936 B2
(45) Date of Patent: May 28, 2019

(54) DISTANCE INTERBODY DEVICE FOR INTRODUCING A BIOMATERIAL TO A VERTEBRAL BODY AND A METHOD OF ITS USE

(71) Applicant: LFC SPOLKA Z O.O., Zielona Gora (PL)

(72) Inventor: Lechoslaw Franciszek Ciupik, Zielona Gora (PL)

(73) Assignee: LFC SPOLKA Z O.O., Zielona Gora (PL)

( * ) Notice: Subject to any disclaimer, the term of this patent is extended or adjusted under 35 U.S.C. 154(b) by 672 days.

(21) Appl. No.: 14/383,508

(22) PCT Filed: Mar. 5, 2013

(86) PCT No.: PCT/PL2013/000027
§ 371 (c)(1),
(2) Date: Sep. 5, 2014

(87) PCT Pub. No.: WO2013/133729
PCT Pub. Date: Sep. 12, 2013

(65) Prior Publication Data
US 2015/0066031 A1    Mar. 5, 2015

(30) Foreign Application Priority Data
Mar. 6, 2012   (PL) .......................... 398316

(51) Int. Cl.
*A61F 2/44* (2006.01)
*A61B 17/16* (2006.01)
(Continued)

(52) U.S. Cl.
CPC .......... *A61F 2/447* (2013.01); *A61B 17/1671* (2013.01); *A61B 17/8811* (2013.01);
(Continued)

(58) Field of Classification Search
CPC ...... A61F 2/4455–2/447; A61F 2/4601; A61F 2/4611; A61F 2002/4475; A61B 17/8811;
(Continued)

(56) References Cited

U.S. PATENT DOCUMENTS 6,800,092 B1    5/2004   Williams et al.
2005/0049590 A1*   3/2005   Alleyne .................. A61F 2/442
                                                    623/17.11
(Continued)

FOREIGN PATENT DOCUMENTS

WO    WO 0049977 A1    8/2000
WO    WO 2005071190 A1   8/2005
(Continued)

OTHER PUBLICATIONS

International Search Report dated Jul. 26, 2013 for co-pending PCT Application No. PCT/PL2013/000027, 4 pages.
Written Opinion of the International Searching Authority dated Jul. 26, 2013 for co-pending PCT Application No. PCT/PL2013/000027, 3 pages.

*Primary Examiner* — Matthew J Lawson
*Assistant Examiner* — Amy R Sipp
(74) *Attorney, Agent, or Firm* — Hovey Williams LLP

(57) ABSTRACT

A distance interbody device for introducing a biomaterial to a vertebral body includes a shaped body and a dispense mechanism operable to dispense biomaterial. The shaped body includes a top side, a bottom side, and a lateral wall forming a peripheral wall that extends between the top and bottom sides. The shaped body is provided with at least one through channel and at least one anchoring element. The through channel includes an internal reservoir for the biomaterial. The through channel passes through the anchoring element to at least one outlet opening located in the at least one anchoring element.

6 Claims, 6 Drawing Sheets

Figure 1:
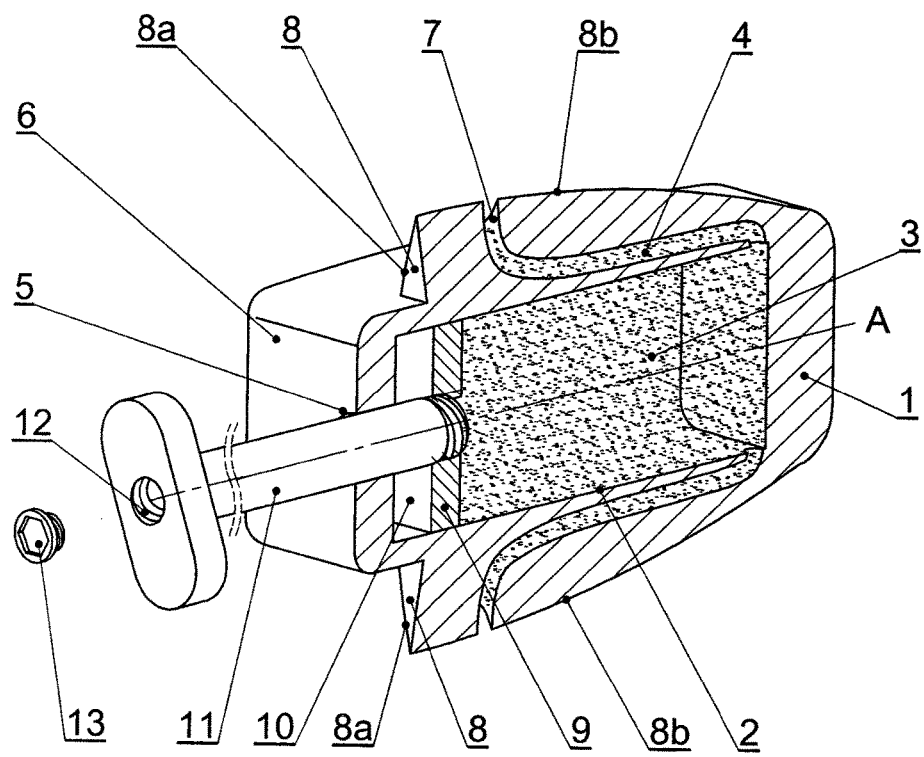

(51) Int. Cl.
*A61B 17/88* (2006.01)
*A61F 2/30* (2006.01)
*A61F 2/46* (2006.01)

(52) U.S. Cl.
CPC ........ *A61B 17/8822* (2013.01); *A61F 2/4455* (2013.01); *A61F 2/30744* (2013.01); *A61F 2/4601* (2013.01); *A61F 2002/3037* (2013.01); *A61F 2002/30266* (2013.01); *A61F 2002/30289* (2013.01); *A61F 2002/30355* (2013.01); *A61F 2002/30484* (2013.01); *A61F 2002/30494* (2013.01); *A61F 2002/30509* (2013.01); *A61F 2002/30515* (2013.01); *A61F 2002/30523* (2013.01); *A61F 2002/30579* (2013.01); *A61F 2002/30583* (2013.01); *A61F 2002/30772* (2013.01); *A61F 2002/30774* (2013.01); *A61F 2002/30777* (2013.01); *A61F 2002/30785* (2013.01); *A61F 2002/30841* (2013.01); *A61F 2002/30845* (2013.01); *A61F 2002/30881* (2013.01); *A61F 2002/30884* (2013.01); *A61F 2002/4475* (2013.01); *A61F 2310/00353* (2013.01)

(58) Field of Classification Search
CPC ............ A61B 17/8822; A61B 17/8805; A61B 17/8625; A61B 17/864; A61B 2017/8655
See application file for complete search history.

(56) References Cited

U.S. PATENT DOCUMENTS

| | | |
|---|---|---|
| 2005/0124989 A1 | 6/2005 | Suddaby |
| 2006/0106459 A1 | 5/2006 | Messerli |
| 2007/0072475 A1* | 3/2007 | Justin .................... A61B 17/025 439/354 |
| 2007/0162132 A1 | 7/2007 | Truckai |
| 2010/0268343 A1 | 10/2010 | Dewey et al. |
| 2011/0004307 A1* | 1/2011 | Ahn ........................ A61F 2/441 623/17.12 |
| 2011/0093074 A1* | 4/2011 | Glerum .................. A61F 2/447 623/17.16 |
| 2011/0264229 A1* | 10/2011 | Donner ............... A61F 2/30988 623/18.11 |
| 2012/0109303 A1 | 5/2012 | Capote |
| 2013/0204371 A1* | 8/2013 | McLuen ............... A61F 2/4455 623/17.16 |
| 2013/0211525 A1* | 8/2013 | McLuen ............... A61F 2/4455 623/17.16 |

FOREIGN PATENT DOCUMENTS

| | | |
|---|---|---|
| WO | WO 2007140315 A2 | 12/2007 |
| WO | WO 2008140551 A2 | 11/2008 |
| WO | WO 2010121149 A2 | 10/2010 |
| WO | WO 2012058356 A2 | 5/2012 |

* cited by examiner

DISTANCE INTERBODY DEVICE FOR INTRODUCING A BIOMATERIAL TO A VERTEBRAL BODY AND A METHOD OF ITS USE

CROSS-REFERENCE TO RELATED APPLICATIONS

This is a National Phase Application pursuant to 37 C.F.R. § 371 of International Application No. PCT/PL2013/000027, filed Mar. 5, 2013, claiming priority from Polish Application No. P-398316, filed Mar. 6, 2012, each of which is incorporated in its entirety by reference herein.

BACKGROUND

1. Field

The invention relates to the distance interbody device for introducing a biomaterial to a vertebral body and a method of its use, which is designed for treatment or biomechanical support of vertebral bodies.

2. Discussion of the Prior Art

From the patent application US2006/0106459 systems and methods of bone treatment are known. One of presented system provides deformable structure, which is introduced in compressed state to the free space of damaged vertebral body using a sleeve. This structure, after filling it with material, which can be a bone cement, expands fulfilling the interior part of damaged vertebra. The structure has got flow-through holes, which cause the structure's expansion in a controlled direction. When the cement bonds, the vertebral body acts like before the damage.

From the patent application US2005/0124989 a bone tamping device for osteoporotic repair is known. The device is provided with a spreading mechanism, having four elongated arms. The spreading mechanism is introduced in a compacted state, through a cannula, into the previously prepared hole in treated bone. After introducing, the spreading mechanism spreads in order to enlarge the cavity in the bone. Next, through the cannula, a cement is introduced into the bone.

From the patent application US 2007/0162132 flexible elongated chain implant and the method of supporting body tissue are known. The implant has a form of chain linked bodies, preferably having a shape of beads made of a bone graft. Previously, using a drill, a hole in a bone is made, or a cavity in the bone is enlarged, and osteoporotic material is removed out of the bone. Using cannula, flexible elongated chain implant is introduced into the cavity in the bone. The implant fulfills the cavity, supporting vertebral endplates and restoring the proper vertebral height.

From the patent application WO2007/140315 system and a method for delivering an agglomeration of solid beads and cement to the interior of a bone in order to form an implant within the bone. The system includes a delivery cannula, which is introduced through a hole into the inner bone. The cannula on its end is provided with a flexible membrane, which is introduced into the bone. Next, using delivery mechanism, through the cannula, solid beans and cement are discharged into the flexible membrane. The membrane expands and fulfills the inner bone, and after bonding cement, normal function of the bone is restored.

Above solutions have disadvantages:
- devices are introduced directly into the bone by performing additional hole in lateral wall of the vertebral body, which causes increased invasiveness,
- devices serves only to repair single vertebral body, don't take into account simultaneous treatment of the whole motion segment or the vertebral body with intervertebral disc.

From the patent application WO2008/140551 fusion device and method of fusion is known. The device has a form of a short sleeve, usually notched on frontal surfaces, and on its lateral surface provided with at least one hole. Through the hole in the lateral surface, cement is delivered, which fulfills the inside of the device and sticks to vertebral endplates, causing stabilization of vertebrae.

This solution has disadvantages:
- the device allows only for vertebral fusion, without possibility of fulfilling vertebrae with filling material, and serves only to fulfill intervertebral space around removed disc,
- the substance fuses only the device with adjacent vertebral endplates.

From the patent application WO2005/071190 a device and method of interbody fusion is known. The device includes a body shaped in order to placement between two vertebrae. The device is provided with injection and delivery holes connected with delivery channels. After performing in vertebra at least one hole, material is injected, and through delivery channels goes to vertebral bodies, causing, after fusion, their stabilization.

SUMMARY

The following summary is provided to indicate the nature of the subject matter disclosed herein. While certain aspects of the present invention are described below, the summary is not intended to limit the scope of the present invention.

With respect to the mentioned state of the art it is a first objective of the present invention to provide an advantageous intervertebral implant. It is a second objective to provide an advantageous method of implanting an intervertebral body.

The first objective is achieved by an intervertebral implant according to claim 1 and the second objective is achieved by a method as claimed in claim 13. The depending claims describe advantageous developments of the invention.

An advantage of the invention over the prior art solutions mentioned above is the provision of a dispenser for a biomaterial within the device.

Free from the inconveniences of the prior art solutions mentioned above is a distance interbody device for introducing a biomaterial to a vertebral body in which, according to the invention, a through channel passes through an anchoring element provided with an outlet hole. The device is provided with at least one dispenser for a biomaterial and with mechanism adducing (administering) the biomaterial.

Typically, at least one anchoring element is located at the top side of the shaped body and/or at least one anchoring element is located at the bottom side of the shaped body.

The at least one anchoring element may comprise lateral faces running at an acute angle relative to each other and an edge where the lateral faces meet each other, where at least one outlet opening is located in the edge. Alternatively or additionally, at least one outlet opening may be located in a lateral face.

Preferably the anchoring element is sliding out of the device.

Preferably the anchoring element is situated in parallel or at the acute angle in relation to the longitudinal axis of the device.

An anchoring element may comprise a cutting knife that is located where the top side or bottom side of the shaped body adjoins to the peripheral wall of the shaped body. If the cutting knife is the leading element of the anchoring element when the device is moved for introducing the anchoring element into the bone tissue the knife facilitates introducing the anchoring element into the bone tissue.

The anchoring element may be provided with a protrusion that protrudes over the outlet opening. Such a protrusion can help to prevent the outlet hole from being blocked by bone tissue.

Preferably the adducing (administering) mechanism is a piston mechanism, a wedge mechanism or a screw (worm) mechanism.

In a method of using the distance interbody device for introducing a biomaterial to a vertebral body according to the invention, during the act of passing through the endplate, it is perforated by the anchoring element of the device. The biomaterial is being introduced to at least one vertebral body from the dispenser (magazine) of the distance interbody device using the adducing (administering) mechanism.

Preferably the vertebral endplate is perforated by the anchoring element situated in parallel to the longitudinal axis of the distance interbody device by sliding this device between vertebral bodies, cutting the endplate of at least one vertebral body, where during introduction of the distance interbody device between vertebral bodies, each of its walls with at least one anchoring element is parallel to the surface made by vertebral endplates.

Preferably the vertebral endplate is perforated by sliding the anchoring element off the distance interbody device cutting the endplate of at least one vertebral body, where during introduction of the distance interbody device between vertebral bodies, each of its walls with the anchoring element is parallel to the surface made by vertebral endplates.

Preferably the vertebral endplate is perforated using anchoring element situated at an acute angle according to the longitudinal axis of the distance interbody device, by rotating this device by 90° about longitudinal axis, cutting the endplate of at least one vertebral body, where during introduction of the distance interbody device between vertebral bodies, each of its walls with at least one anchoring element is perpendicular to the surface made by vertebral endplates.

Advantages of the solution according to the invention are:
provision of the device with material dispenser,
possibility of additional charge of the dispenser after return to the initial position of the adducing mechanism, without the necessity of withdrawal the device out of interbody space,
possibility of treatment the whole motion segment, not only the single vertebra.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Figure 2:
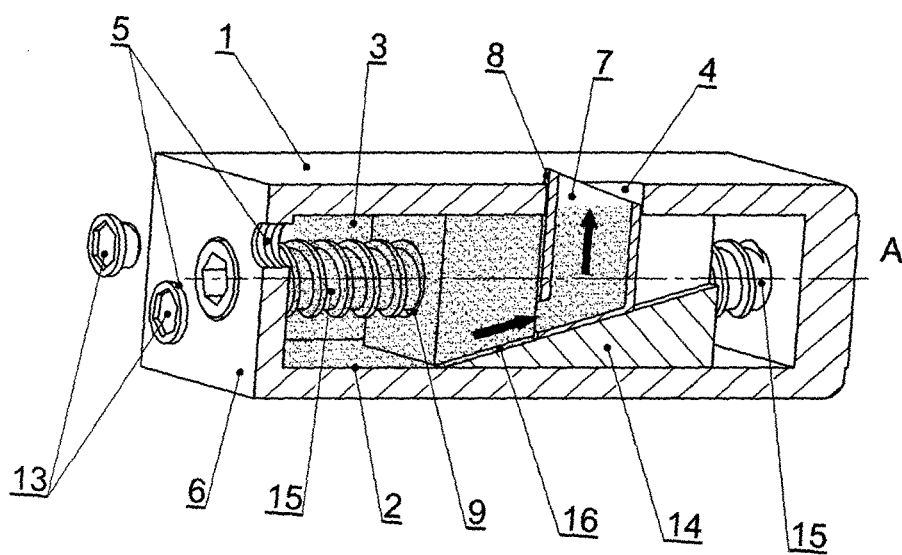
Figure 3:
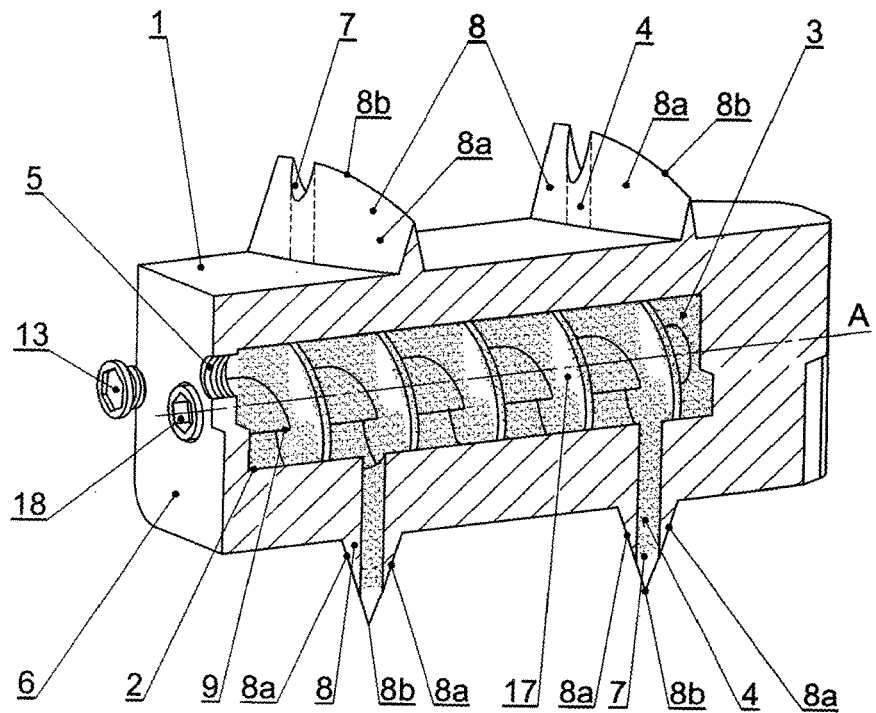
Figure 4:
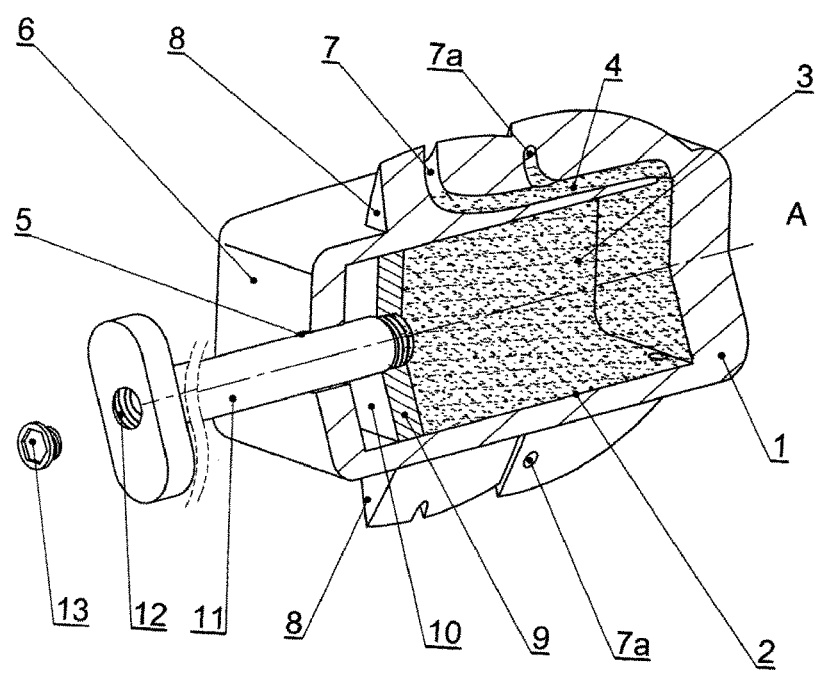
Figure 5:
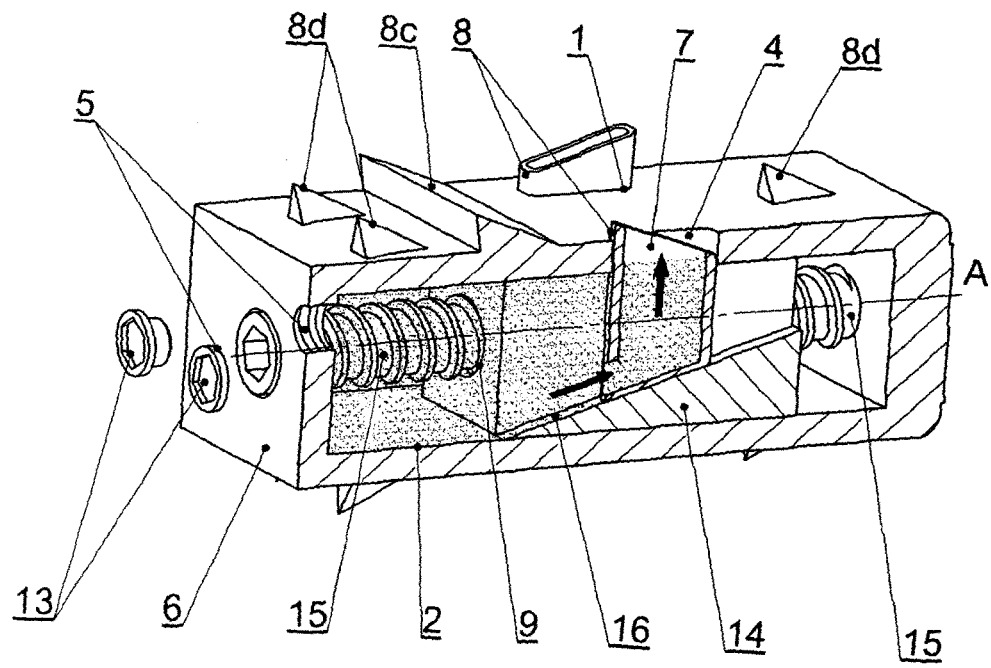
Figure 6:
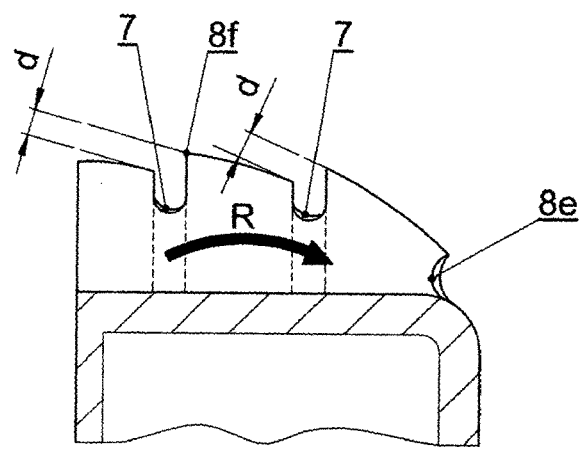
Figure 7:
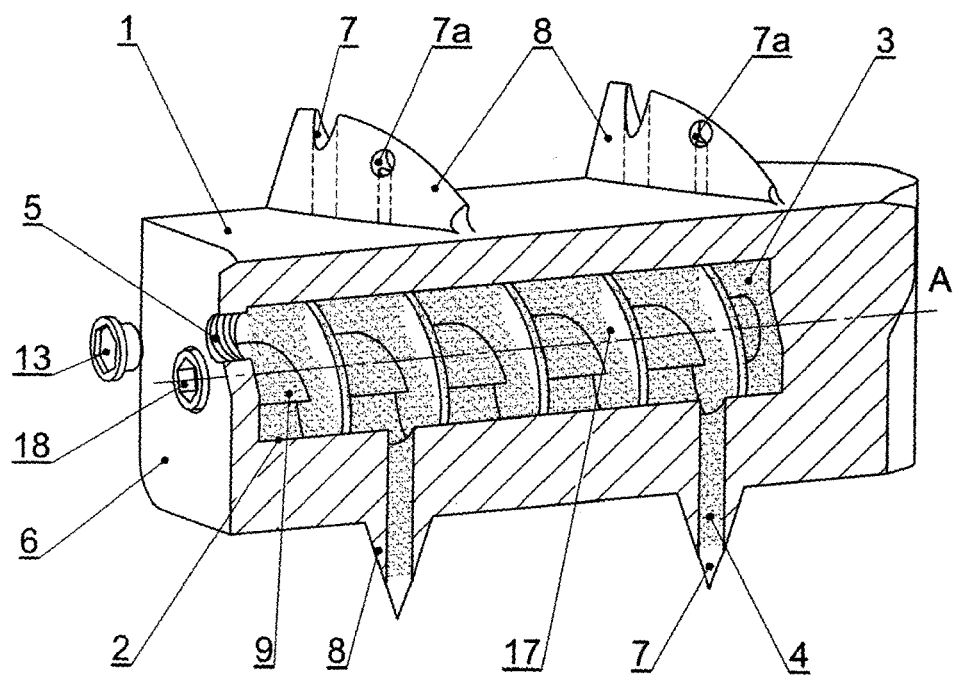

Distance interbody device for introducing a biomaterial to a vertebral body and a method of its use will be explained on a base of figures, wherein:

FIG. 1 illustrates in a cross-section a distance interbody device constructed in accordance with a first embodiment of the present invention, with the distance interbody device including two anchoring elements situated in parallel to the longitudinal axis of the device, and an adducing mechanism comprising a piston mechanism, FIG. 2 illustrates in a cross-section a distance interbody device constructed in accordance with a second embodiment of the present invention, with the distance interbody device including one anchoring element slidable out of the body, and an adducing mechanism comprising a wedge adducing mechanism, FIG. 3 illustrates in a cross-section a distance interbody device constructed in accordance with a third embodiment of the present invention, with the distance interbody device including four anchoring elements situated at an acute angle in relation to the longitudinal axis of the device and an adducing mechanism comprising a screw (worm) adducing mechanism, FIG. 4 illustrates a cross section of a distance interbody device constructed in accordance with a fourth embodiment of the present invention, with the distance interbody device being similar to the embodiment shown in FIG. 1, but also presenting an outlet opening in a lateral face of the anchoring element, FIG. 5 illustrates a cross section of a distance interbody device constructed in accordance with a fifth embodiment of the present invention, with the distance interbody device being similar to the embodiment shown in FIG. 2, but having an alternative configuration of anchoring elements that includes two anchoring elements slidable out of the body, FIG. 6 illustrates a fragmentary cross section of a distance interbody device constructed in accordance with a sixth embodiment of the present invention, with the distance interbody device being similar to the embodiment shown in FIG. 3, but having an alternative anchoring element comprising a cutting knife, and FIG. 7 illustrates a cross section of a distance interbody device constructed in accordance with a seventh embodiment of the present invention, with the distance interbody device being similar to the embodiment shown in FIG. 3, but having alternative anchoring elements that present side faces with additional outlet openings.

DETAILED DESCRIPTION OF THE PREFERRED EMBODIMENTS

The distance interbody device for introducing a biomaterial to a vertebral body can be regarded as an intervertebral implant in form of a shaped body 1. The shaped body 1 comprises a top side 1a for being placed at an end plate of a first vertebral body and a bottom side 1b for being placed at an end plate of a second vertebral body. A peripheral wall or side wall 6 extends between the top side 1a and the bottom side 1b and forms a lateral wall of the shaped body 1.

At least one anchoring element 8a is located at the top side and at least one anchoring element 8b is located at the bottom side. However, it is also possible that two or more anchoring elements 8a, 8b are present at the top side 1a and/or at the bottom side 1b. Moreover, it is also conceivable that only one of the top side and the bottom side is equipped with at least one anchoring element, although having anchoring elements at both the top side 1a and the bottom side 1b is preferred.

Inside the shaped body 1, there is a reservoir of biomaterial. Hence, the shaped body 1 provides a dispenser 2 of a biomaterial 3. The biomaterial 3 can be for example a cement in a form of biocompatible PMMA polymer, which during injection is mild/soft, and hardens after introduction to the vertebral body. Through the dispenser 2 passes a through channel 4, which is provided with an inlet hole 5 in a side wall 6 and an outlet hole 7, through which the biomaterial 3 is introduced to the vertebral body. Moreover, the reservoir is formed by an enlarged section of the through channel. The through channel 4 passes through the anchoring element 8, and the outlet hole 7 is situated in the anchoring element 8.

The device presented on FIG. 1 is a first embodiment of the invention. This embodiment is provided with two anchoring elements 8 situated in parallel to the longitudinal axis A of the device. Each anchoring element 8 comprises lateral faces 8a running at an acute angle relative to each other and an edge 8b that is formed by the merging lateral faces 8a. At least one outlet opening 7 for biomaterial 3 is located in the edge 8b. However, additionally or alternatively at least one outlet opening could be present in a lateral face 8a of the anchoring element 8, or even in both lateral faces. A modification of the first embodiment in which an additional outlet opening 7a is present in a lateral face 8a of the anchoring element is shown in FIG. 4.

The adducing mechanism 9 of the biomaterial 3 is the piston mechanism consisting of a throng 10 and a piston rod 11. The piston rod 11 is hollow and equipped with an inlet hole 12 closed with a plug 13. Before introduction of the device between vertebral bodies, the dispenser 2 is filled through the hollow piston rod 11 with the biomaterial 3. Next, the device is inserted between vertebral bodies such that its walls with anchoring elements 8 are shifted in parallel to the surface of vertebral endplates. After introduction of the device between vertebral bodies, its anchoring elements 8 immerse in vertebral endplates so deep, that after displacement of the piston rod 11 from the dispenser 2, the biomaterial 3 using the adducing mechanism 9 is shifting through outlet holes 7 to vertebral bodies.

A second embodiment of the distance interbody device is shown in FIG. 2. Like in the first embodiment, the shaped body 1 comprises a top side 1a for being placed at an end plate of a first vertebral body and a bottom side 1b for being placed at an end plate of a second vertebral body. A peripheral wall or side wall 6 extends between the top side 1a and the bottom side 1b and forms a lateral wall of the shaped body 1.

As distinguished from the distance interbody device of the first embodiment, in the device of the second embodiment presented in FIG. 2, the anchoring element 8 is sliding out, and the adducing mechanism 9 of the biomaterial 3 is a wedge mechanism consisting of a wedge 14 and a driving element 15, which enables shifting the wedge 14 within the device. The device has got in its side wall 6 two inlet holes 5 closed with plugs 13. The device is introduced between vertebral bodies such that each wall with the anchoring element 8 is shifted along the vertebral endplate. After introducing the device between vertebral bodies, the driving element 15, which is in form of a screw in the present embodiment, drives the wedge 14 which is, in the present embodiment, equipped with a thread cooperating with the screw. With this construction, rotating the screw moves the wedge towards the side wall 6 with the two inlet holes 5. Hence, the wedge 14 causes, that its wall 16 forces sliding the anchoring element 8 out of the device. In addition, moving the wedge 14 towards the side wall 6 with the two inlet holes 5 reduces the space in the reservoir and hence forces the biomaterial 3 out of the outlet hole while the anchoring element 8 is sliding out of the shaped body 1. As a consequence, the anchoring element 8 passes through the vertebral endplate and from the dispenser 2, through the outlet hole 7 the biomaterial 3 is introduced to the vertebral body.

Although in the present embodiment the biomaterial 3 is introduced to the vertebral body while the anchoring element 8 is moved out of the shaped body it is also possible to have two different mechanisms for moving the anchoring element 8 out of the shaped body 1 and for forcing the biomaterial 3 out of the outlet hole 7. If different mechanisms for moving the anchoring element 8 out of the shaped body 1 and for forcing the biomaterial 3 out of the outlet hole 7 are present the dispenser may be filled after the anchoring element 8 has been moved out of the shaped body 1. In contrast thereto, when only one mechanism is present for moving the wedge 14 out of the shaped body 1 and for forcing the biomaterial 3 out of the outlet hole 7 simultaneously the reservoir is filed before the wedge 14 is moved out of the shaped body 1.

Although there is only one anchoring element 8 in the present embodiment, which is moved out of the top wall 1a of the shaped body 1, there may be more than one such anchoring element 8. In particular, there may be an anchoring element 8 that can be moved out of the top wall 1a of the shaped body 1 and another anchoring element 8 that can be moved out of the bottom wall 1b of the shaped body 1. Moreover there may also be more than anchoring element 8 that can be moved out of the top wall 1a of the shaped body 1 and/or more than one anchoring element 8 that can be moved out of the bottom wall 1b of the shaped body 1. In addition, further anchoring elements which are not movable may be present on the top wall 1a of the shaped body 1 and/or on the bottom wall 1b of the shaped body. A modified embodiment with two anchoring elements 8 that can be moved out of the top wall 1a of the shaped body 1 and with additional anchoring elements 8c, 8d that are located on the top wall 1a of the shaped body 1 is shown in FIG. 5. As additional anchoring elements there are edges 8c and spikes 8d present on the top wall 1a. Please note that the shaped body could also include one or more anchoring elements that can be moved out of the bottom wall and/or additional anchoring elements 8c, 8d that are located on the bottom wall.

A third embodiment of the distance interbody device is shown in FIG. 3. Like in the first and second embodiments, the shaped body 1 comprises a top side 1a for being placed at an end plate of a first vertebral body and a bottom side 1b for being placed at an end plate of a second vertebral body. A peripheral wall or side wall 6 extends between the top side 1a and the bottom side 1b and forms a lateral wall of the shaped body 1.

The device presented on FIG. 3 has got anchoring elements 8 situated at an angle of about 75° to the longitudinal axis A of the device. These anchoring elements form sections of a helix-like structure. The adducing mechanism 9 of the biomaterial 3 is the screw/worm mechanism consisting of a screw 17 and a driving roller 18. The inlet hole 5 is closed with the knob 13. The device, with the biomaterial 3 in the dispenser 2 is introduced between vertebral bodies such that its walls with anchoring elements 8 are perpendicular to the surface made by vertebral endplates. After the device is introduced, it is rotated by 90° about the longitudinal axis A of the device, which causes, that anchoring elements 8 immerse in vertebral endplates. Rotation of the driving roller 18 transfers the biomaterial 3 to vertebral bodies through outlet holes 7.

In order to support cutting into the bone tissue of the vertebral endplates, each anchoring element 8 may comprises a cutting knife 8e, as it is shown in FIG. 6, which shows a modification of the embodiment shown in FIG. 3 in a cross-sectional view. Please note that the section of FIG. 6 runs perpendicular to the cross section of FIG. 3. Such a cutting knife is advantageously located where the top side 1a or the bottom side 1b of the shaped body 1 adjoins to the peripheral wall 6.

To prevent the outlet hole 7 from being blocked by bone tissue during the insertion of the distance interbody device the anchoring element may be provided with a protrusion that protrudes over the outlet opening 7. In the embodiment shown in FIG. 6 the protrusion is formed by a protruding section 8f of the edge 8b that precedes the outlet hole 7 in the direction R of rotating the distance interbody device during implantation between two vertebra end plates. The protruding section 8f protrudes by a distance d over the edge section following the outlet opening 7 in the direction R of rotation. By this measure, the depth of the cut provided in the bone tissue of a vertebral end plate by rotating the distance interbody device is larger than the length the edge section following the outlet opening 7. As a consequence, the edge section following the outlet opening 7 does not extend to the bottom of the cut so that the outlet opening is not blocked by bone tissue. Instead, the cut forms a channel for the biomaterial 3. A protruding section 8f as has been described above may also be present in the edges 8b of the anchoring elements 8 of the embodiments shown in FIGS. 1 and 4

In a further modification of the embodiment shown in FIG. 3 or in a modification of the embodiment shown in FIG. 6 one or more additional outlet openings 7a may be present in at least one side face 8a of an anchoring element 8. Such a modification is shown in FIG. 7.

The following clauses are a nonexhaustive summary the invention:

1. Distance interbody device for introducing a biomaterial to a vertebral body, in a form of shaped body provided with at least one through channel with an inlet hole in the lateral wall from the side of the surgical approach and at least one anchoring element, is characterized with that, the through channel (4) passes through the anchoring element (8) provided with the through hole (7) it is provided with at least one dispenser (magazine) (2) for the biomaterial (3) and mechanism (9) adducing (administering) the biomaterial (3).
2. Distance interbody device according to the clause 1, is characterized with that, the anchoring element (8) is sliding out (can slide out) of the device.
3. Distance interbody device according to the clause 1, is characterized with that, the anchoring element (8) is situated parallel to the longitudinal axis (A) of the device.
4. Distance interbody device according to the clause 1, is characterized in that, the anchoring element (8) is situated at the acute angle in relation to the longitudinal axis (A) of the device.
5. Distance interbody device according to the clause 1, is characterized in that, the adducing (administering) mechanism (9) is a piston mechanism.
6. Distance interbody device according to the clause 1, is characterized in that, the adducing (administering) mechanism (9) is a wedge mechanism.
7. Distance interbody device according to the clause 1, is characterized in that, the adducing (administering) mechanism (9) is a screw (worm) mechanism.
8. A method of using the distance interbody device for introducing a biomaterial to a vertebral body, where between vertebral bodies the distance interbody device is introduced, which is provided with at least one through channel; next, through the endplate of at least one vertebral body the biomaterial is introduced where,
   during the act of passing through the endplate, it is perforated by the anchoring element (8) of the device defined in clauses 1-7, and the biomaterial (3) is being introduced to at least one vertebral body from the dispenser (magazine) (2) of the distance interbody device using the adducing (administering) mechanism (9).
9. A method according to clause 8, where,
   the vertebral endplate is perforated by the anchoring element (8) situated parallel to the longitudinal axis (A) of the distance interbody device by shifting this device between vertebral bodies, cutting the endplate of at least one vertebral body, where during introduction of the distance interbody device between vertebral bodies, each of its walls with the anchoring element (8) is parallel to the surface made by vertebral endplates.
10. A method according to clause 8, where,
    the vertebral endplate is perforated by sliding the anchoring element (8) out of the distance interbody device cutting the endplate of at least one vertebral body, where during introduction of the distance interbody device between vertebral bodies, each of its walls with the anchoring element (8) is parallel to the surface made by vertebral endplates.
11. A method according clause 8, where
    the vertebral endplate is perforated using anchoring element (8) situated at an acute angle according to the longitudinal axis (A) of the distance interbody device, by rotating this device 90° about longitudinal axis (A), cutting the endplate of at least one vertebral body, where during introduction of the distance interbody device between vertebral bodies, each of its walls with at least one anchoring element (8) is perpendicular to the surface made by vertebral endplates.

The invention claimed is:

1. A distance interbody device to be introduced to a vertebral body, said distance interbody device comprising:
   a biomaterial;
   a shaped body including a top side for being placed at an end plate of a first vertebral body, a bottom side for being placed at an end plate of a second vertebral body, and a lateral wall forming a peripheral wall that extends between the top side and the bottom side,
   said shaped body being provided with at least one through channel with an inlet hole in the lateral wall from a side of a surgical approach and at least one anchoring element,
   said through channel including an internal reservoir for the biomaterial,
   said through channel passing through the at least one anchoring element to at least one outlet opening located in the at least one anchoring element,
   said at least one anchoring element extending outwardly from one of the top side and the bottom side, in a direction perpendicular to the one side, to present an edge spaced outwardly from the one side, said edge and said one side cooperatively defining a maximum perpendicular dimension of the at least one anchoring element measured in the perpendicular direction, said at least one anchoring element presenting a minimum parallel dimension measured at the one side in a direction parallel thereto, said parallel dimension being less than the perpendicular dimension, with the at least one anchoring element being configured to perforate the endplate of one of the first and second vertebral bodies along the edge; and a wedge dispensing mechanism at least partly inside the reservoir and operable to dispense the biomaterial therefrom, said wedge dispensing mechanism including a wedge shiftable within the device to reduce the space in the reservoir and thereby force the biomaterial out of the reservoir via the at least one outlet opening, said at least one anchoring element being arranged in the shaped body such that it can slide out of the shaped body, said wedge engaging the at least one anchoring element to dispense the biomaterial via the at least one outlet opening while moving the at least one anchoring element out of the shaped body.

2. The distance interbody device as claimed in claim 1, said at least one anchoring element being located at the top side of the shaped body and/or at the bottom side of the shaped body.

3. The distance interbody device as claimed in claim 1, said at least one anchoring element being situated parallel to a longitudinal axis of the device.

4. The distance interbody device as claimed in claim 1, said edge at least partly extending about and at least partly defining the outlet opening.

5. The distance interbody device as claimed in claim 4, said edge extending endlessly about the outlet opening.

6. The distance interbody device as claimed in claim 1, said shaped body including a plurality of anchoring elements that include the at least one anchoring element, said plurality of anchoring elements extending from the one side in the perpendicular direction to present respective edges, with the plurality of anchoring elements being spaced apart from each other along the one side.

* * * * *